US009816067B2

(12) United States Patent
Ophardt

(10) Patent No.: US 9,816,067 B2
(45) Date of Patent: Nov. 14, 2017

(54) AUTOMATED BIOLOGICAL GROWTH AND DISPENSING APPARATUS

(71) Applicant: OP-Hygiene IP GmbH, Niederbipp (CH)

(72) Inventor: Heiner Ophardt, Arisdorf (CH)

(73) Assignee: OP-Hygiene IP GmbH, Niederbipp (CH)

(*) Notice: Subject to any disclaimer, the term of this patent is extended or adjusted under 35 U.S.C. 154(b) by 716 days.

(21) Appl. No.: 14/213,254

(22) Filed: Mar. 14, 2014

(65) Prior Publication Data

US 2014/0206063 A1 Jul. 24, 2014

Related U.S. Application Data

(60) Continuation of application No. 13/485,177, filed on May 31, 2012, now abandoned, which is a division of
(Continued)

(30) Foreign Application Priority Data

Sep. 4, 2003 (CA) ..................... 2439645

(51) Int. Cl.
*C12N 1/20* (2006.01)
*C12M 1/00* (2006.01)
(Continued)

(52) U.S. Cl.
CPC ............... *C12N 1/20* (2013.01); *C12M 23/28* (2013.01); *C12M 23/38* (2013.01); *C12M 23/40* (2013.01); *C12M 23/44* (2013.01); *C12M 27/02* (2013.01)

(58) Field of Classification Search
USPC ......... 435/252.1, 286.5, 286.7, 289.1, 291.6; 366/196
See application file for complete search history.

(56) References Cited

U.S. PATENT DOCUMENTS 3,396,844 A * 8/1968 Millhiser .................. B03B 5/34
209/724
3,924,007 A 12/1975 Driessen et al.
(Continued)

FOREIGN PATENT DOCUMENTS

EP 0353898 2/1990
EP 0901812 3/1999
(Continued)

OTHER PUBLICATIONS

Chisti et al.; Aeration and Mixing in Vortex Fermenters; Journal of Chemical Technology and Biotechnology; Feb. 1993; pp. 331-336; vol. 58; Society of Chemical Industry.

*Primary Examiner* — Michael Hobbs
*Assistant Examiner* — Liban Hassan
(74) *Attorney, Agent, or Firm* — Thorpe North & Western LLP

(57) ABSTRACT

An automated biological growth and dispensing apparatus utilizing a modular growing tank which is removable for replacement by another growing tank. Mechanisms for the delivery of air, water and/or nutrients are adapted to permit the growing tank to be readily coupled and uncoupled for easy and inexpensive replacement. Mechanisms for agitation may be integral and removable with the growing tank or may be adapted for a quick connection and disconnection with the growing tank. The growing tank may be disposable and each new growing tank may be provided as a sealed container including a starting amount of a biomass and/or nutrient.

20 Claims, 12 Drawing Sheets

Related U.S. Application Data application No. 12/289,720, filed on Nov. 3, 2008, now Pat. No. 8,206,973, which is a continuation-in-part of application No. 10/928,109, filed on Aug. 30, 2004, now abandoned.

(51) Int. Cl.
  *C12M 3/00*  (2006.01)
  *C12M 1/06*  (2006.01)

(56) References Cited

U.S. PATENT DOCUMENTS

| | | |
|---|---|---|
| 3,933,585 A | 1/1976 | McAleer |
| 3,992,270 A | 11/1976 | Lemarinel et al. |
| 4,143,999 A | 3/1979 | Ryall |
| 4,305,673 A | 12/1981 | Herbst |
| 4,519,959 A | 5/1985 | Takeuchi |
| 4,888,294 A | 12/1989 | Van Wezel |
| 5,075,234 A | 12/1991 | Tunac |
| 5,143,543 A | 9/1992 | Reid |
| 5,267,791 A | 12/1993 | Christian |
| 5,306,420 A | 4/1994 | Bisconte |
| 5,376,114 A | 12/1994 | Jarvik |
| 5,417,550 A | 5/1995 | Kasai et al. |
| 5,447,866 A | 9/1995 | Runyon |
| 5,470,151 A | 11/1995 | Walthall et al. |
| 5,683,575 A | 11/1997 | Yates et al. |
| 5,836,482 A | 11/1998 | Ophardt et al. |
| 5,866,002 A | 2/1999 | Yates |
| 5,921,913 A | 7/1999 | Siess |
| 6,029,101 A | 2/2000 | Yoshida et al. |
| 6,109,780 A | 8/2000 | Lesniak |
| 6,168,949 B1 | 1/2001 | Rubenberger |
| 6,271,027 B1 | 8/2001 | Sarem |
| 6,306,658 B1 | 10/2001 | Turner et al. |
| 6,335,191 B1 | 1/2002 | Kiplinger |
| 6,343,724 B1 | 2/2002 | Ophardt et al. |
| 6,391,638 B1 * | 5/2002 | Shaaltiel ............ C12M 23/14 435/289.1 |
| 6,579,712 B1 | 6/2003 | Rothweiler |
| 6,589,018 B2 | 7/2003 | Chen |
| 6,706,518 B2 | 3/2004 | Lorenz et al. |
| 6,854,876 B2 | 2/2005 | Dickson, Jr. |
| 8,206,973 B2 | 6/2012 | Ophardt |
| 2001/0051371 A1 | 12/2001 | Kiplinger et al. |
| 2002/0163855 A1 | 11/2002 | Beebe |
| 2002/0179525 A1 | 12/2002 | Shaffer |
| 2003/0145727 A1 | 8/2003 | Murai |
| 2005/0032032 A1 | 2/2005 | Pearce et al. |

FOREIGN PATENT DOCUMENTS

| | | |
|---|---|---|
| EP | 0943677 | 9/1999 |
| GB | 583499 | 12/1946 |
| GB | 665921 | 2/1952 |
| GB | 1223418 | 2/1971 |
| GB | 1393654 | 5/1975 |
| GB | 2305936 | 4/1997 |
| JP | 05-192699 | 8/1993 |
| JP | H 05/192699 | 8/1993 |
| JP | 07286596 | 10/1995 |
| JP | H07-286596 | 10/1995 |
| JP | 2002/239306 | 8/2002 |
| JP | 2002239306 | 8/2002 |

* cited by examiner

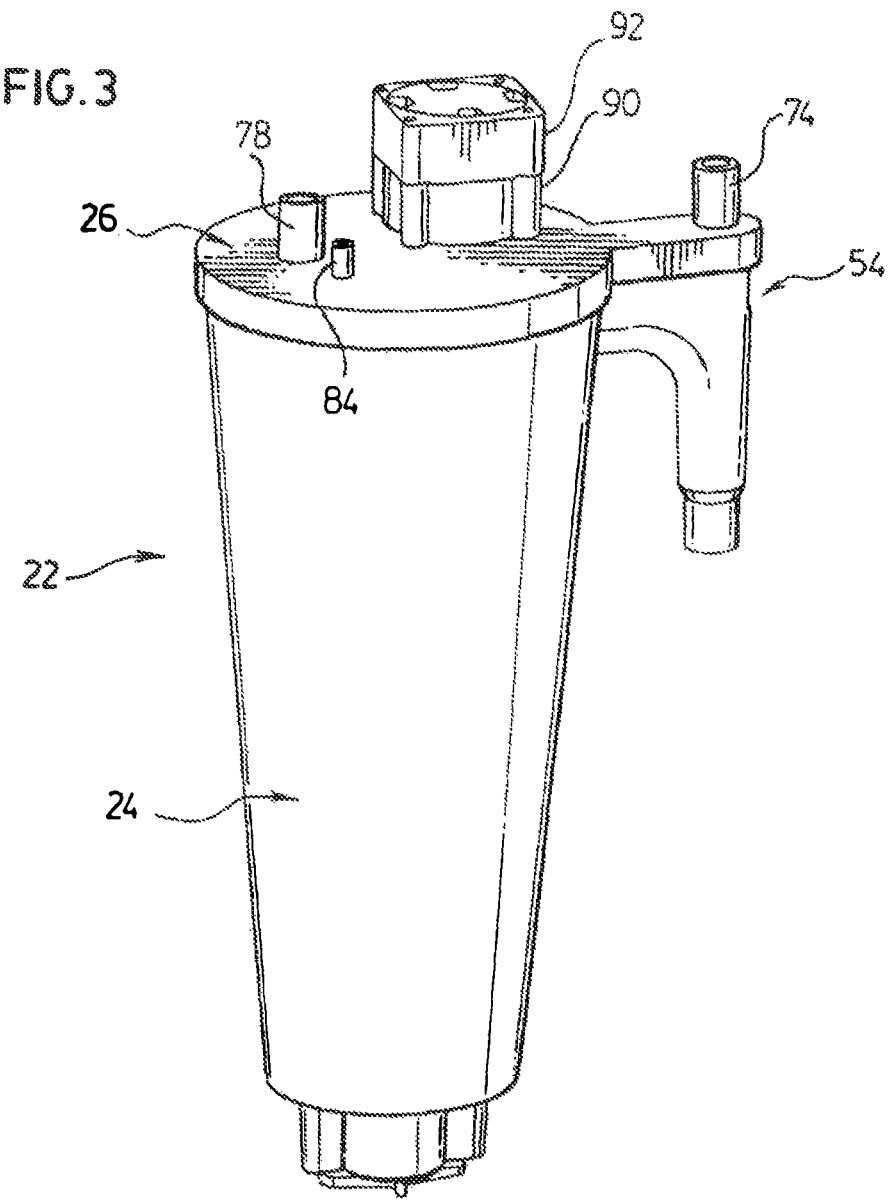

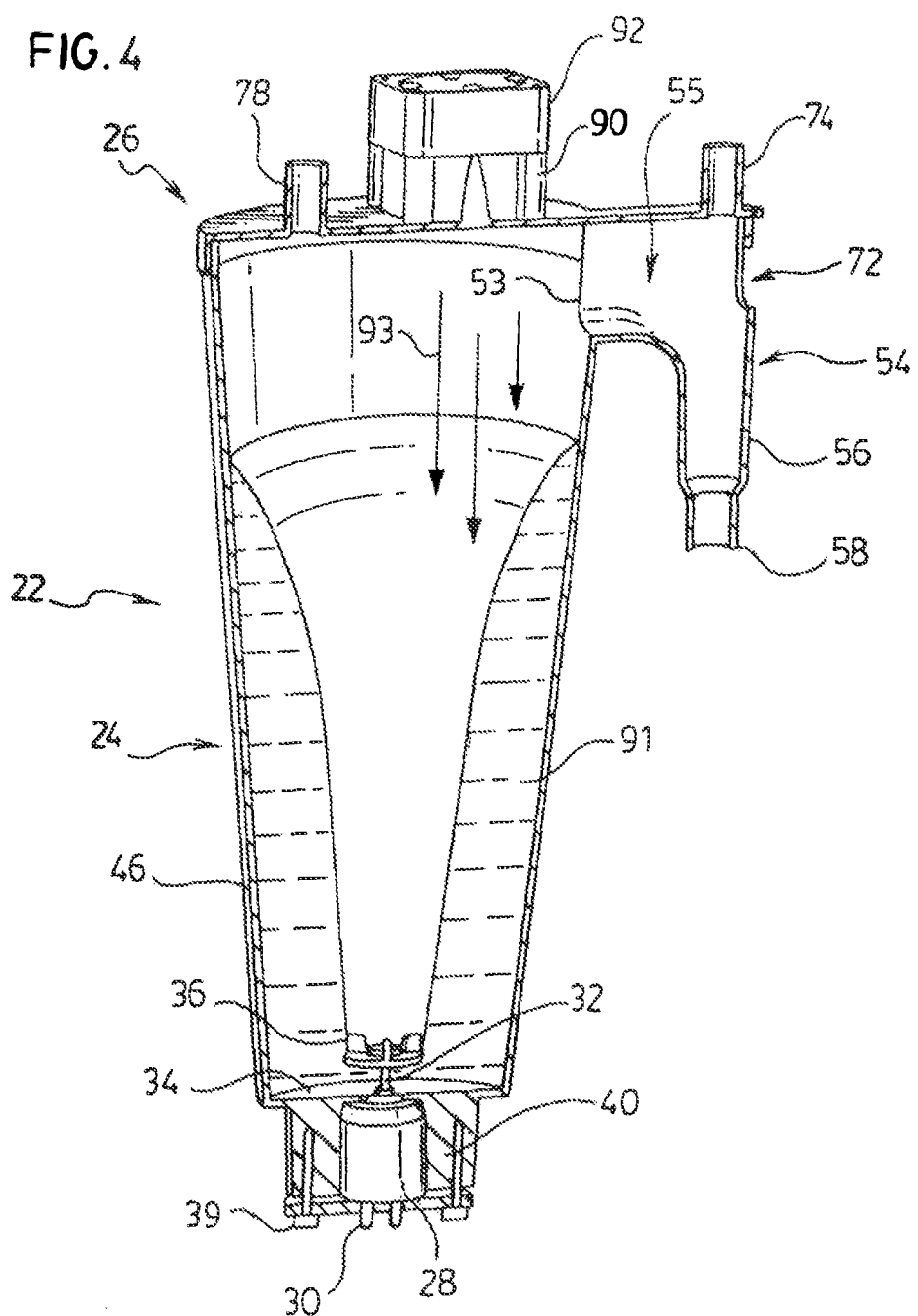

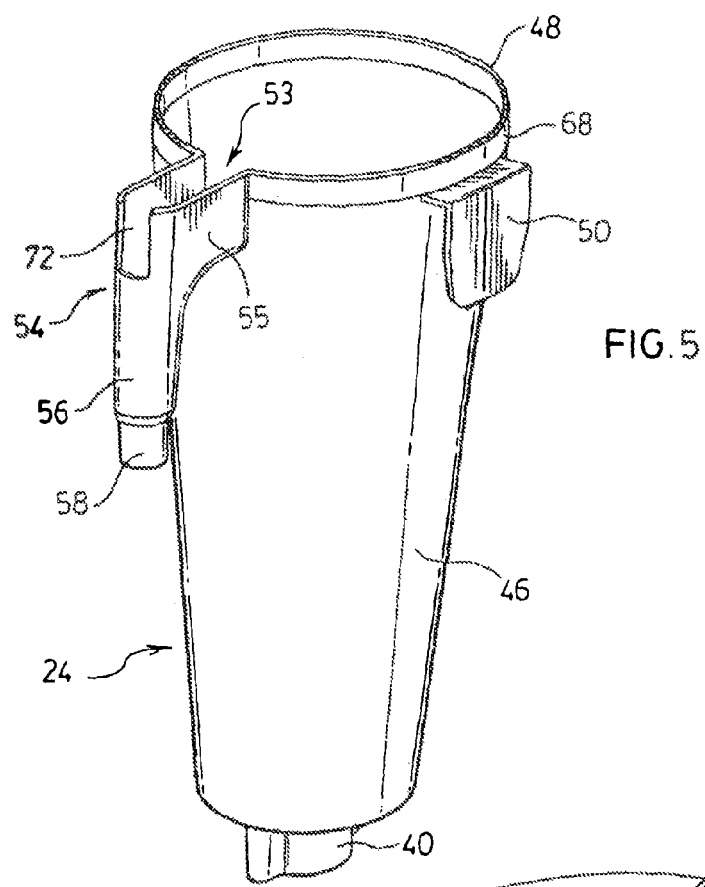
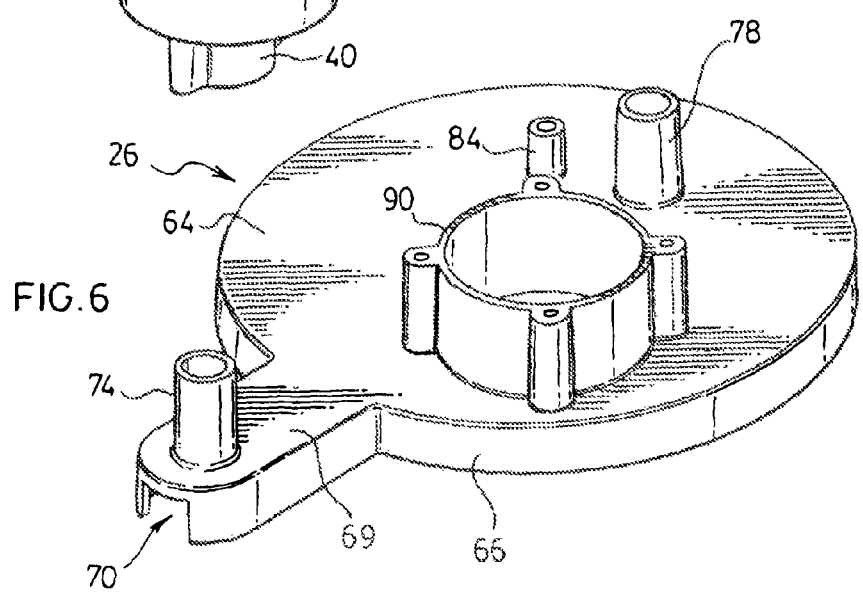

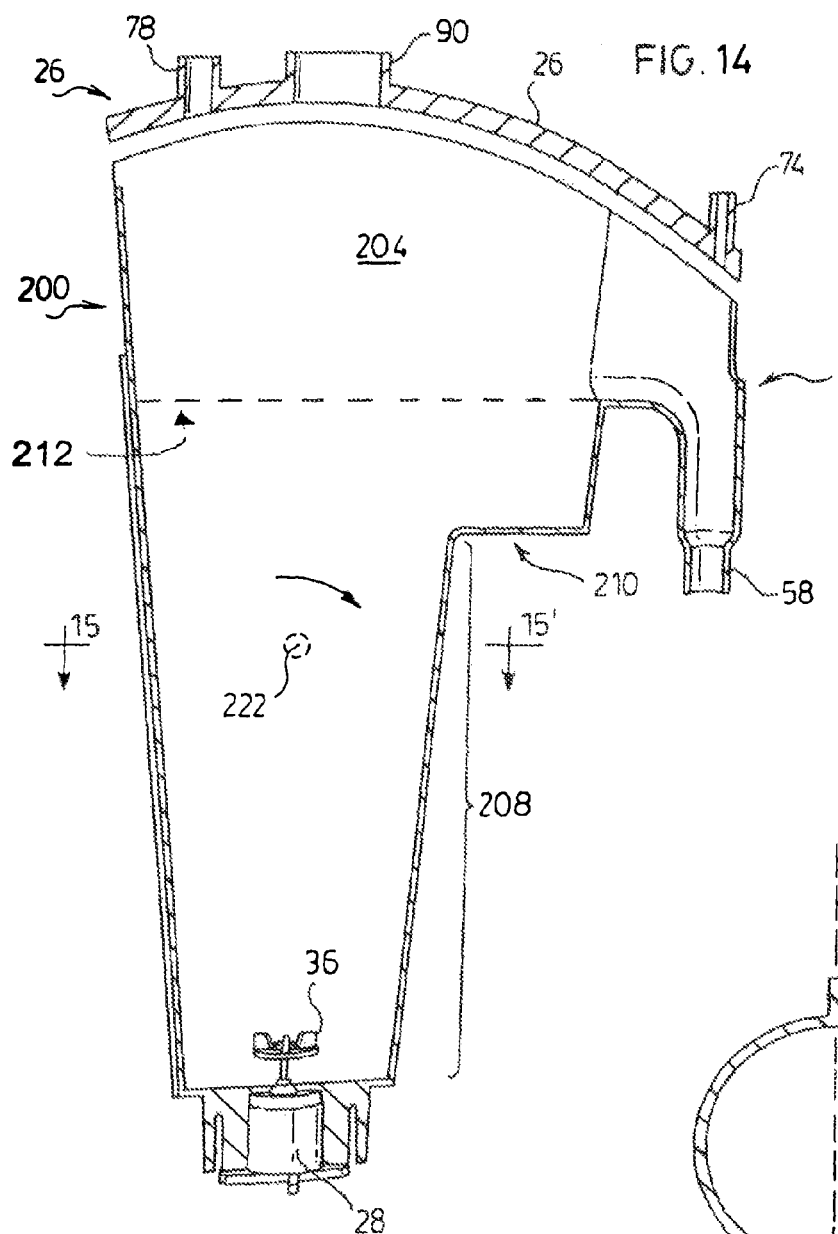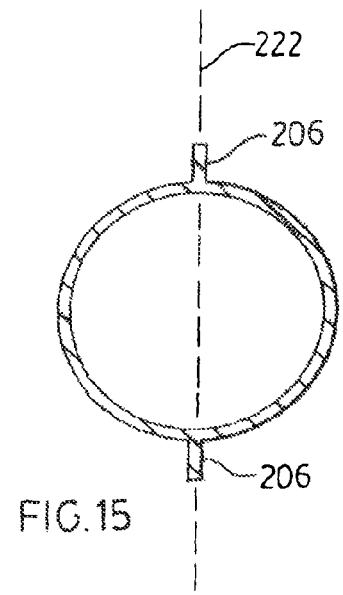
FIG. 14
FIG. 15

AUTOMATED BIOLOGICAL GROWTH AND DISPENSING APPARATUS

RELATED APPLICATIONS

This application is a continuation of U.S. patent application Ser. No. 13/485,177, filed May 31, 2012 which is a divisional of U.S. patent application Ser. No. 12/289,720 filed Nov. 3, 2008 which issued to U.S. Pat. No. 8,206,973 which is a continuation-in-part of U.S. patent application Ser. No. 10/928,109 filed Aug. 30, 2004, abandoned.

SCOPE OF THE INVENTION

The present invention relates to an automated biological growth and dispensing system and, more particularly, to an automatic bacteria cultivation and dispensing system adapted for incubating bacteria from a starter population and for dispensing bacteria to perform a desired utility such as removal of grease from grease traps.

BACKGROUND OF THE INVENTION

Automated systems and methods for growing bacteria are known. Some systems utilize starter bacteria and nutrients in a powder form. Difficulties exist in respect of the storage and/or dispensing of the starter bacteria and nutrients. For example, when the starter bacteria and/or nutrients are in powder form, moisture can cause the powder to solidify and prevent ease of handling and dispensing. Maintenance of the starter bacteria and nutrients within an enclosure containing the device necessarily increases moisture within the enclosure above that in the ambient air and increases difficulties in handling and dispensing the starter bacteria and nutrients. Temperature concerns arise in that the starter bacteria and nutrients may need to be stored at temperatures which are above or below ambient under certain conditions.

Known automated systems for growing bacteria typically utilize a bio-generator in which the bacteria and nutrients are placed and grown on a batch basis. Typically, feed devices provide additional nutrients, water and air. Typically, pumps are used to dispense and feed. After use of the bio-generator as to grow the bacteria and dispense the bacteria over a period of time, the bio-generator requires emptying of all the contents from the bio-generator and cleaning the bio-generator before a new batch of biomass may be added and cultivated. Cleaning by merely washing the system out with water is imperfect and does not provide for adequate cleaning. Cleaning is important to ensure a new batch of bacteria is not contaminated by previously grown bacteria. Cleaning is labour-intensive and is difficult given the relatively complex nature of previously known bio-generators and their associated nutrient, water and air feed devices and pumps. Periodic cleaning of the bio-generator therefore is expensive and the labour costs involved alone can offset any overall cost savings resulting from use of the bio-generator compared to alternate mechanisms to the bio-generator such as, for example, merely pumping out a grease trap periodically.

Known bio-generators are relatively complex in their mechanical arrangement and, therefore, generally a single bio-generator is provided with starter bacteria introduced to include a number of different bacteria cultures. A disadvantage has been appreciated that, over time, different of the bacteria strains will become dominant in the bio-generator due to an inherent tendency of some of the bacterial strains to grow as compared to others having regard to the nature of the nutrients, the nature of the temperature and concentration of the nutrients and the like. Thus, over a period of time during which the bio-generator is operated and before it may be cleaned and a new batch commenced, the relative proportions of the bacteria in the mixture may vary against that which may be preferred and this can occur even if there may be relatively accurate attempts to control conditions such as temperature.

Previously known bio-generators typically have dispensing and/or re-circulating pumps to circulate the fluid containing the water, bacteria and nutrients. Such re-circulating pumps involve tubes and conduits through which the liquid may pass which tubes and conduits are extremely difficult and time consuming to clean and necessarily involve junctures and joints where, over time, mechanical failure can arise.

Known automated biological growth and dispensing systems are typically not adapted for remote site operation as, for example, where there is no power source or source of pressurized water. Known automated biological growth and dispensing systems typically have relatively high power consumption and are not adapted for operation over extended periods such as 14 to 30 days driven by batteries.

Known automated biological growth and dispensing systems typically require periodic handling of starter bacteria and nutrients as, for example, to start a batch or to recharge a hopper or container from which bacteria and nutrients are dispensed. Such handling is disadvantageous in respect of potential contamination of the starter bacteria and nutrients and/or of the environment about the dispensing system.

Previously known automated biological growth and dispensing systems utilize a combination of starter bacteria and nutrients in dry powdered form. This has the disadvantage that such dry powder is difficult to handle and dispense to each new batch. In addition, the relative proportions of bacteria to nutrients is preset in the powder, and cannot be adjusted.

SUMMARY OF THE INVENTION

To at least partially overcome these disadvantages of previously known devices, the present invention provides an automated biological growth and dispensing system utilizing a modular growing tank which is removable for replacement by another growing tank. Mechanisms for the delivery of air, water and/or nutrients are adapted to permit the growing tank to be readily coupled and uncoupled for easy and inexpensive replacement. Mechanisms for agitation may be integral and removable with the growing tank or may be adapted for a quick connection and disconnection with the growing tank. The growing tank may be disposable and each new growing tank may be provided as a sealed container including a starting amount of a biomass and/or nutrient.

Each individual growth and dispensing system may be provided with a plurality of growing tanks so as to provide cumulatively a desired system capacity and/or to provide for growing of different biomass and/or bacteria in each tank. Preferably, nutrients to be added to the growing tank include nutrients in a liquid form for ease of storage separately from the bacteria and for ease of dispensing.

in one aspect, the present invention provides a simplified construction for an automated biological growth and dispensing system.

In another aspect, the present invention provides a disposable one-piece growing tank for ease of connection and disconnection to an automated biological growth and dispensing system.

In another aspect, the present invention provides a replaceable one-piece growing tank which is provided with a starting amount of biomass and/or nutrients.

In another aspect, the present invention provides an automated biological growth and dispensing system adopting a plurality of replaceable and/or disposable growing tanks.

In another aspect, the present invention provides a growing tank for an automated biological growth and dispensing system incorporating an inexpensive disposable motor coupled thereto and replaceable therewith.

In another aspect, the present invention provides a growing tank for an automated biological growth and dispensing system in which air is provided by a simple air fan.

Accordingly, in one aspect, the present invention provides an automated batch process useful for growing bacteria comprising repeating a batch cycle comprising the steps of:

(i) introducing a batch starter population of bacteria, water and nutrients, and growing the bacteria in fluid from the batch starter population to a utility population within a predetermined interval and thereafter, (ii) repeating a sub-cycle of:

(a) dispensing a dispensed portion of bacteria to perform a desired utility while maintaining a remaining portion of bacteria, and (b) growing bacteria in the remaining portion to a utility population with the addition of additional water and/or nutrients to the tank, (iii) followed by, after a number of said sub-cycles, discharging all bacteria from the batch and repeating the batch cycle steps (i) to (iii), the process carried out in an apparatus comprising:

a modular bio-generation tank having a top, a bottom, a water inlet for entry of water into the tank, an air inlet for entry of air into the tank, a nutrient inlet for entry of nutrients into the tank, and a tank outlet for flow of fluid from the tank, an agitation mechanism for agitating fluid in the tank, an air delivery system for delivery of air via the air inlet into the tank into contact with fluid in the tank, a water delivery system for delivery of water via the water inlet into the tank, a nutrient delivery system for delivery of nutrient via the nutrient inlet into the tank, the tank being removable, wherein after each batch cycle and as a step in the next batch cycle the tank used in the previous batch cycle is removed and a tank for the next cycle is coupled in its place such that a batch starter population of bacteria for each cycle is in a tank free of bacteria from a previous batch cycle.

In a further aspect, the present invention provides an apparatus for growing bacteria comprising:

a) a base assembly, and b) a removable modular tank unit;

the tank unit coupling to and removable from the base apparatus as for replacement by a similar modular unit, the tank unit comprising a modular bio generation tank, an agitation motor and an impeller, the tank having a top, a bottom, a side wall extending upwardly from the bottom, and a tank outlet for flow of fluid from the tank at a height above the bottom, the tank outlet comprising an overflow outlet for flow of fluid from the tank under gravity when fluid in the tank is at a height above a height of the overflow outlet, the top of the tank is open upwardly providing a tank inlet opening, the agitation motor coupled to the bottom of the tank, the motor coupled to the impeller in the tank through the bottom of the tank to rotate the impeller in the tank, the impeller disposed in the tank for rotation about the axis directing fluid impinging on the impeller radially outwardly into the side wall and up the side wall thereby creating a standing vortex, the base assembly comprising a delivery manifold, a water delivery system, an air delivery system, a nutrient delivery system, a power source for the motor and a controller, the delivery manifold removably coupled to and uncoupled from the tank unit via an upper quick connect and disconnect arrangement engaging the top of the tank such that when coupled to the tank unit the manifold comprises a top lid covering the tank inlet opening, the manifold carrying a water inlet for delivery of water into the tank when the manifold is coupled to the tank unit, an air inlet for delivery of air into the tank when the manifold is coupled to the tank unit, and a nutrient inlet for delivery of nutrients into the tank when the manifold is coupled to the tank unit;

the water delivery system delivering water to the water inlet, the air delivery system delivering air to the air inlet, the nutrient delivery system delivering nutrients to the nutrient inlet, the power source removably coupled to and uncoupled from to tank unit via a lower quick connect and disconnect arrangement for coupling to and uncoupling from the tank unit by engaging the motor at the bottom of the tank such that when coupled to the tank unit the power source provides power to the motor to rotate the impeller, wherein the impeller is rotatable about the axis to create the standing vortex of fluid in the tank to raise the fluid in the tank up the side wall to heights within the tank which increase with increased speed of rotation of the impeller and the impeller is rotatable at speeds which raise the fluid in the tank up the side wall in the tank to heights above the tank outlet for discharge of fluid from the tank via the tank outlet, the controller controlling operation of the motor to mix fluid in the tank by rotating the impeller at speeds which do not raise the fluid in the tank to the height of the tank outlet, and to discharge fluid from the tank by rotating the impeller at speeds which raise the fluid in the tank to heights above the tank outlet.

In another aspect, the present invention provides a method of dispensing fluid from a container, the container having a base, side walls extending upwardly from the base and an exit opening at a height above the base, the method characterized in comprising:

providing fluid in the container at a height below the exit opening, providing an impeller in the container rotatable about an axis to discharge fluid impinging on the impeller, rotating the impeller for a period of time at speeds which create and maintain a standing vortex in the container with a height of the standing vortex being below a height of the exit opening, and to dispense fluid from the container, increasing the speed of rotation of the impeller to increase the height of the standing vortex to a height of the exit opening such that fluid above the exit opening exits the container via the exit opening.

BRIEF DESCRIPTION OF THE DRAWINGS

Further aspects and advantages of the present invention will become apparent from the following description taken together with the accompanying drawings in which:

FIG. 3 is a perspective view of the assembled growing tank and lid shown in FIG. 1;

FIG. 4 is a cross-sectional side view through the growing tank assembly shown in FIG. 3;

FIG. 5 is a perspective view of merely the growing tank of FIG. 3;

FIG. 6 is a perspective view of the lid for the tank shown in FIG. 1;

FIG. 14 is a cross-sectional view similar to FIG. 4 of a tank which is gimballed;

FIG. 15 is a cross-section along section line 15-15' in FIG. 14; and

DETAILED DESCRIPTION OF THE DRAWINGS

Figure 1:
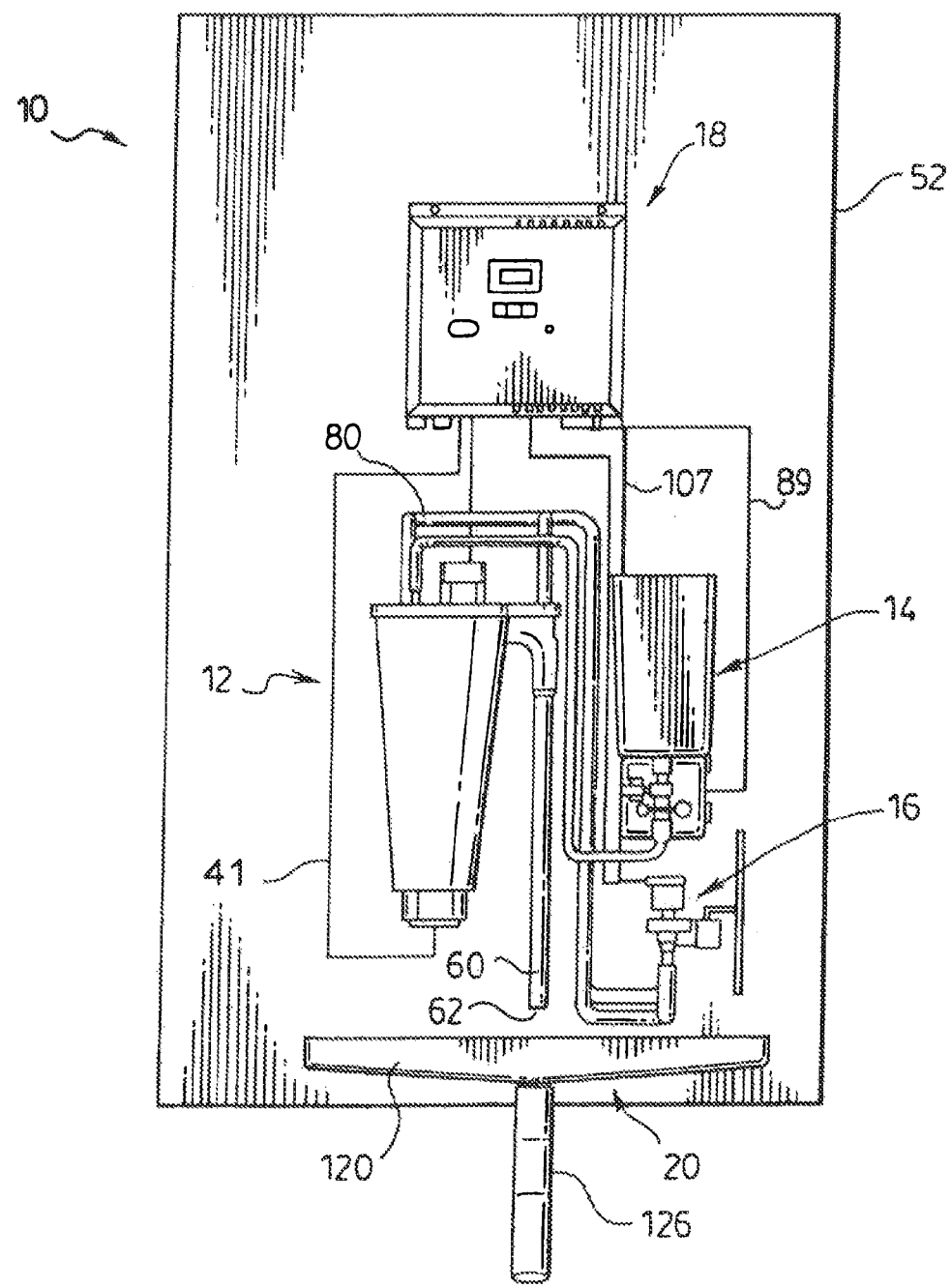
FIG. 1 is a front view of a first embodiment of an automated biological growth and dispensing system in accordance with the present invention.

Reference is made to FIGS. 1 to 4 which illustrate a preferred embodiment of an automated biological growth and dispensing system 10 in accordance with the present invention. The system comprises a bio-generator 12, a feedstock delivery system 14, a water delivery system 16, a controller 18 and a drain system 20.

The bio-generator 12 includes a vessel 22 formed from a growing tank 24 and a lid 26. An agitating motor 28 is coupled to the growing tank 24 at its bottom and serves to mix fluids within the growing tank 24. The motor 28, as seen in FIG. 6, has been provided as an inexpensive DC motor mounted to the bottom of the growing tank 24 with a shaft 32 which extends through a bottom wall 34 of the growing tank 24 journalled therein and carrying an impeller 36. A seal is provided between the shaft 32 and the bottom wall 34 as by a gasket.

The growing tank 24 includes a downwardly extending circular boss 40 with a central bore therein to receive the motor 28. Threaded fasteners 39 engage a plate on the motor 28 to removably secure the motor 28 within the bore. On activation of the motor 28, the shaft 32 and impeller 36 are rotated to cause fluid within the tank 24 to be rotated in one direction forming a relatively deep vortex as illustrated schematically in FIG. 4 towards increasing the opportunity for oxygen in air above the fluid to be absorbed by the fluid. The motor 28 is mounted coaxially within the tank 24 as believed is preferred, however, this is not necessary. In the preferred embodiment, the motor 28 has two contact pins 30 and is adapted for quick connection and disconnection as by a removable wiring plug with electrical wiring 41 which couples the motor 28 to the controller 18.

The growing tank 24 is shown as having a generally frusto-conical configuration with a side wall 46 extending upwardly from the bottom wall 34 and outwardly therefrom as a segment of a cone. The side wall 46 presents an inner surface which is circular in cross-section and enlarges in diameter from the bottom wall 34 to an upper open end 48 of the tank 24. The tank 24 may have other shapes.

As seen in FIG. 1, the system 10 is preferably mounted on a mounting board which may comprise a rear panel 52 of a housing which would include, while not shown in the drawings, a removable housing cover comprising top, bottom, two sides and a front surface to contain the system 10 and protect it from exposure to the elements and the like. Mechanisms may or may not be provided to control the temperature and humidity within the housing. As best seen in FIG. 5, a mounting flange 50 is provided adapted for engagement with a complementary tank support bracket so as to permit the tank 24 to be removably mounted.

While not shown in the drawings, the rear panel 52 of the housing is provided with a mounting bracket complementary to the tank mounting flange 50 such that the tank 24 may be easily, removably mounted to and removed from the rear panel 52 for replacement as by another tank 24 of a similar configuration.

The side wall 46 of the tank 24 carries an overflow outlet spout 54 on one side thereof. The outlet spout 54 extends from an opening 53 in the side wall as a horizontally extending upwardly opening passageway 55 which ends at a downwardly extending tube 56 open at an exit outlet 58. A drain hose 60 is coupled to the tube 56 about the exit outlet 58 and extends downwardly to outlet 62.

Reference is made to FIG. 6 which shows the tank lid 26 which is adapted to be removably secured to tie tank 24 in a snap fit relation. The lid 26 has a top 64 and a depending flange 66 extending downwardly therefrom such that the flange 66 may engage in a snap fit removable relation onto a raised annular rim 68 about the upper open end 48 of the tank 24 as seen in FIG. 5. The top 64 includes a circular portion with an arm 69 extending therefrom which arm 69 overlies the outlet spout 54. The flange 66 at the end of the arm 69 is cut away as an opening 70 above an air gap opening 72 on the outlet spout 54. Together the opening 70 and air gap opening 72 provide a safety overflow outlet which, in a failure condition as, for example, should the tube 56 become clogged, will permit fluid from the tank 24 to flow outwardly through the air gap opening 72 and drop under gravity into the drain system 20. Air gap opening 72 is provided with a view to preventing the material in the tank 24 or overflowing therefrom from rising to a level which would come into engagement with or to contaminate the water delivery system carried by the lid 26.

As best seen in FIG. 6, the arm 69 of the lid 26 carries a drain water inlet port 74. The drain water inlet port is coupled via a drain water tube 76 to a drain water inlet valve 79 of the water delivery system 16 as shown in FIGS. 2 and 8.

Figure 2:
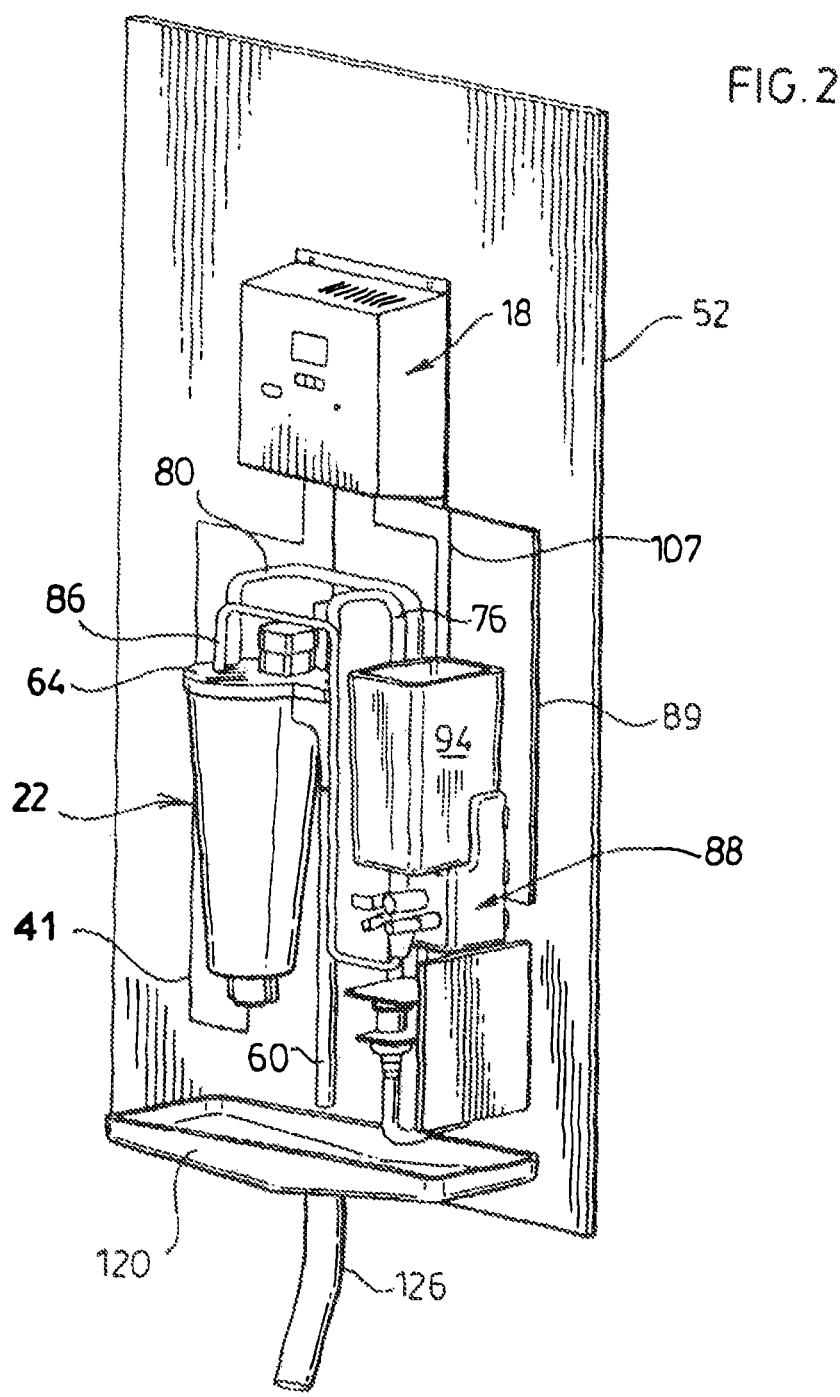
FIG. 2 is a front perspective view of the system of FIG. 1.
Figure 8:
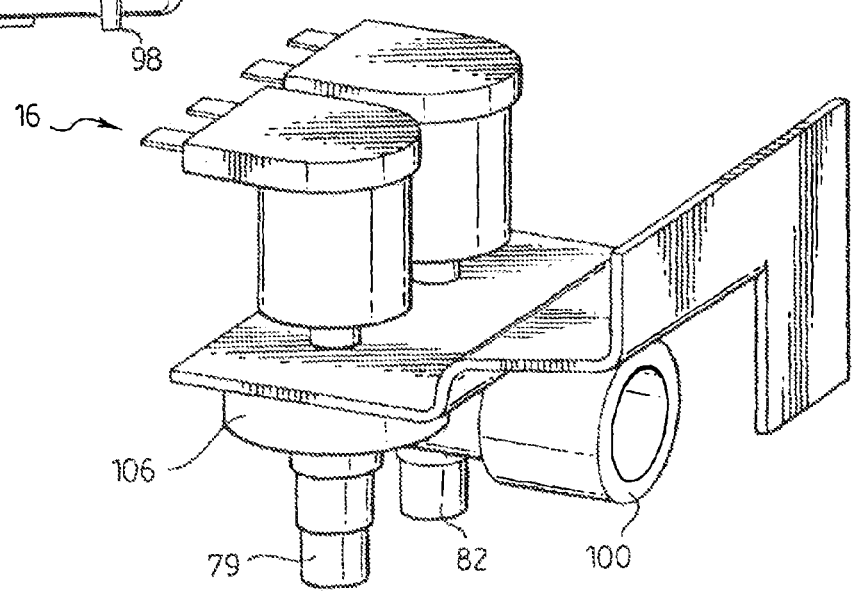
FIG. 8 is a perspective view of the water inlet valve shown in FIG. 1.

The top 64 includes a tank water inlet port 78 which is coupled via a tank water tube 80 coupled to an inlet valve 82 of the water delivery system 16 as shown in FIGS. 2 and 8.

The top 64 includes a feedstock port 84 coupled by a feedstock tube 86 to the feedstock dispensing unit 88 of the feedstock delivery system 14.

The lid 26 carries an upstanding air fan mounting flange 90 upon which an air fan 92 is mounted as best seen in FIG. 3. The air fan 92 comprises a known air fan which has a housing, an electric motor mounted in the housing, a shaft coupled to the electric motor and an impeller carried on the shaft such that activation of the motor rotates the impeller to draw air through the housing pass the motor and to blow air down into the tank 24. Excess air may exit via the air gap opening 72. As schematically shown in FIG. 4, air represented by arrows 93 is directed downwardly from the air fan 92 to make contact with the fluid 91 in the tank to increase the exchange of gases, notably, oxygen into the fluid.

Figure 7:
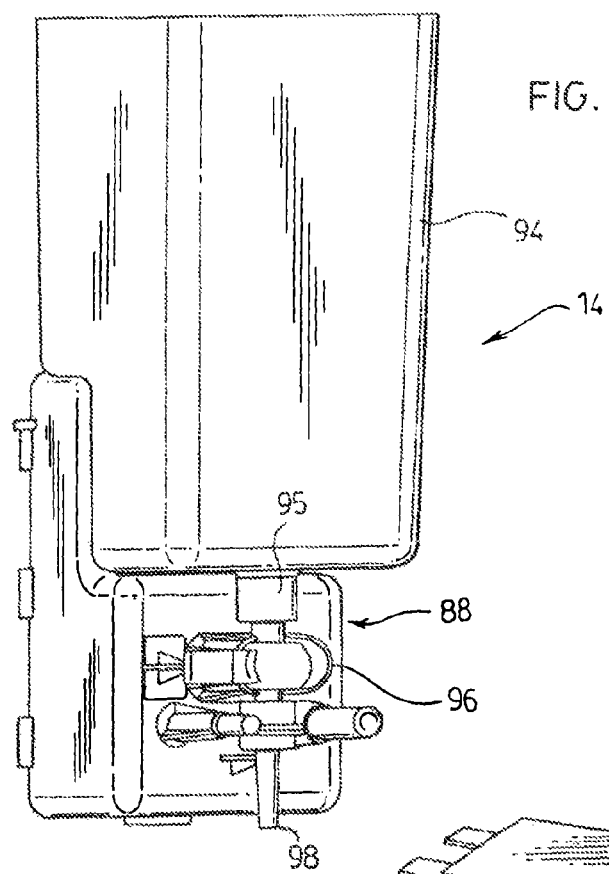
FIG. 7 is a front perspective view of the feedstock dispensing unit shown in FIG. 1.

Reference is made to FIG. 7 which shows the feedstock delivery system 14 comprising a feedstock reservoir 94 with an outlet 95 coupled to a dispensing pump 96 whose outlet 98 is coupled to the feedstock delivery tube 86 shown in FIG. 2 for delivery of feedstock into the growing tank 24 through the feedstock port 84 in the lid 26. The dispensing pump 96 preferably is a gear pump as described in U.S. Pat. Nos. 5,836,482 and 6,343,724, the disclosures of which are incorporated herein by reference. In such a gear pump, the gear pump is driven by an electric motor. The gear pump is preferably of a construction to minimize energy usage so as to permit it to be driven as by batteries. The feedstock dispensing unit 88 and its pump 96 are connected by wires 89 to the controller 18 as seen in FIG. 1.

The feedstock delivery system 14 comprising the reservoir 94, the gear pump 96 and the motor associated with the gear pump are commercially available as an integrated unit. The preferred feedstock delivery system 14 may be selected from commercially available automated fluid dispensers such as are useful in dispensing hand soap. The feedstock is preferably to be provided as a liquid which can be easily dispensed by the feedstock dispensing unit 88. One preferred liquid is a concentrated sugar feedstock. The concentrated sugar solution may have other nutrients other than sugar as, for example, in solution or in colloidal suspension. Preferably, the liquid feedstock does not include bacteria or other active biomass and thus will be relatively stable.

The feedstock delivery system 14 is adapted for control by the controller 18 to provide controlled quantities of feedstock into the growing tank 24 as and when desired.

The feedstock dispensing unit 88 is adapted to be secured to the rear panel 52 in a conventional manner and for removal as necessary. The feedstock reservoir 94 is shown in FIG. 2 as having an open top to facilitate periodic filling of the feedstock reservoir 94 with the feedstock. Alternatively, the feedstock reservoir may be removable as either a collapsible or rigid reservoir which may be periodically replaced rather than being refilled for reuse.

The water delivery system 16 is illustrated in FIG. 8 as including an inlet coupling 100 to which a conduit, not shown, is to be coupled so as to provide water from a source of pressurized water.

The inlet coupling 100 directs water via a water manifold 106 to two separate valves, namely a solenoid controlled tank water inlet valve 82 and a solenoid controlled drain water inlet valve 79. Each of these valves have respective outlets coupled to the tank water tube 80 or drain water tube 76 to deliver either tank water to the tank 24 via tank water inlet port 78 or drain water to the drain water port inlet 74. The valves 79 and 82 are well known electrically controlled valves which are movable between open and closed positions and may be electrically connected via wiring 107 to the controller 18 for control so as to move between open and closed positions as may be desired.

Figure 9:
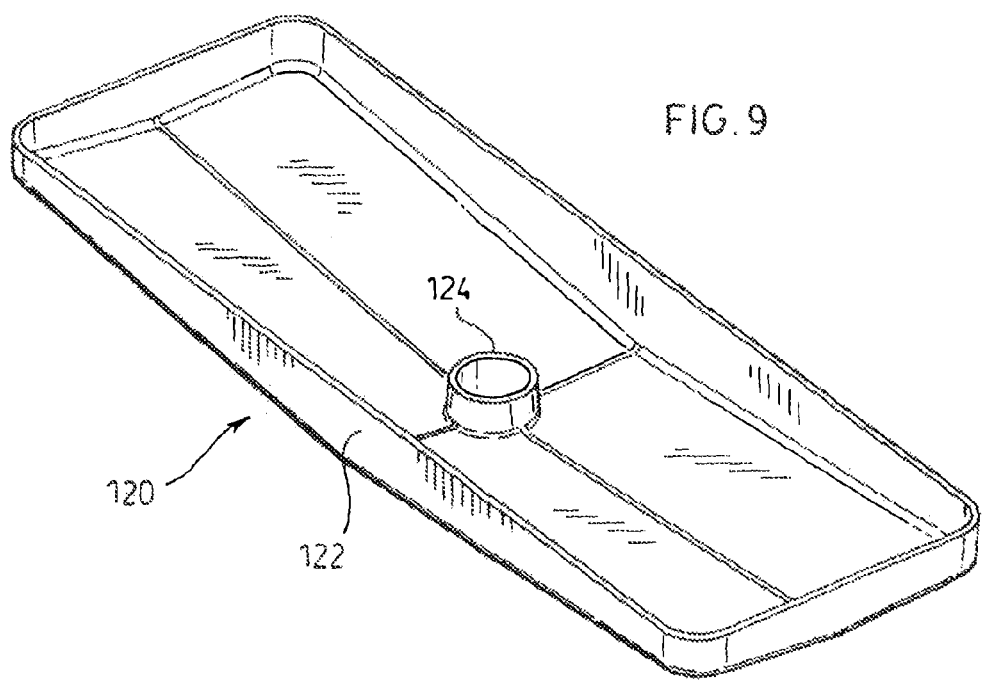
FIG. 9 is a top perspective view of the drain pan shown in FIG. 1.

The drain system 20 comprises a drain pan 120 as best seen in FIG. 9. The drain pan as shown is provided underneath the entirety of the bio-generator 12, feedstock delivery system 14 and water delivery system 16 and encompasses a cross-sectional area underneath the same so as to catch any fluids or other materials which might, under gravity, drip downwardly. In this regard, the drain pan covers a suitable cross-sectional area underneath the components from which drippings are to be caught. The drain pan 120 has an upstanding peripheral flange 122 to catch any drippings or dispensed fluids and to direct the same in the manner of a hopper or funnel towards a drain pan outlet 124 which is coupled by a drain hose 126 shown in FIG. 2 to a location where the biomass to be delivered from the system 10 is desired as, for example, to a drain in a restaurant as where the biomass may digest grease in the grease trap. In normal operation of the system 10, biomass which is grown within the tank 24 is periodically dispensed from the growing tank and via the tank drain hose 126 such liquid is dispensed from the outlet 62 of the tank outlet hose 60 is disposed above the drain pan 120 and drops through an air gap between the drain hose outlet 62 onto the drain pan 120 and, hence, is delivered as to a restaurant drain for usage. The drain hose outlet 62 is spaced above the drain pan 120 so as to provide an air gap thereto and prevent contamination into the tank drain hose 60 of materials from the drain pan 120.

Figure 11:
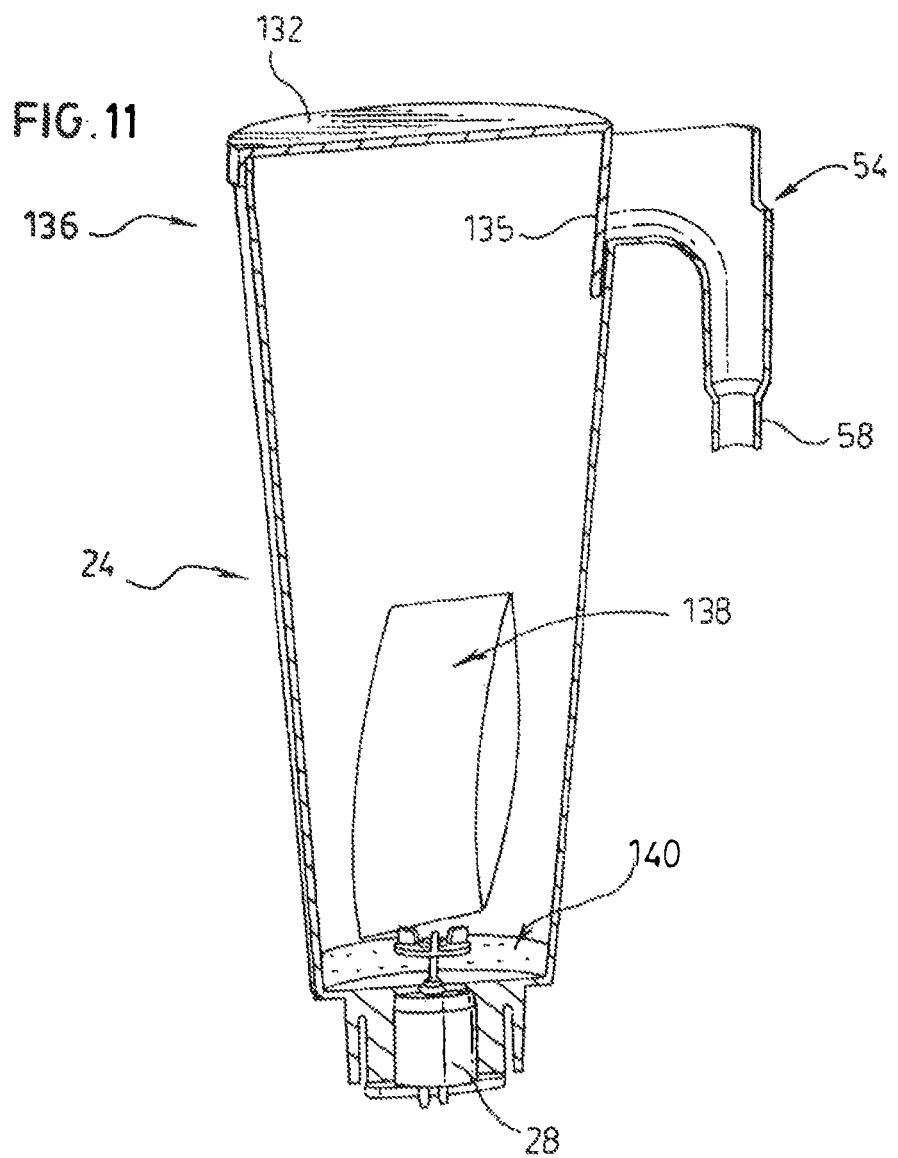
FIG. 11 is a view similar to FIG. 4 of a tank of FIG. 5 with a closure cap of FIG. 10.

FIG. 11 illustrates a modular replacement bio-generator 136 comprising a growing tank 24 sealed by a closure cap 132, with the motor 28 and its impeller 36 attached to the growing tank 24 and including inside a package 138 and material 140.

Figure 10:
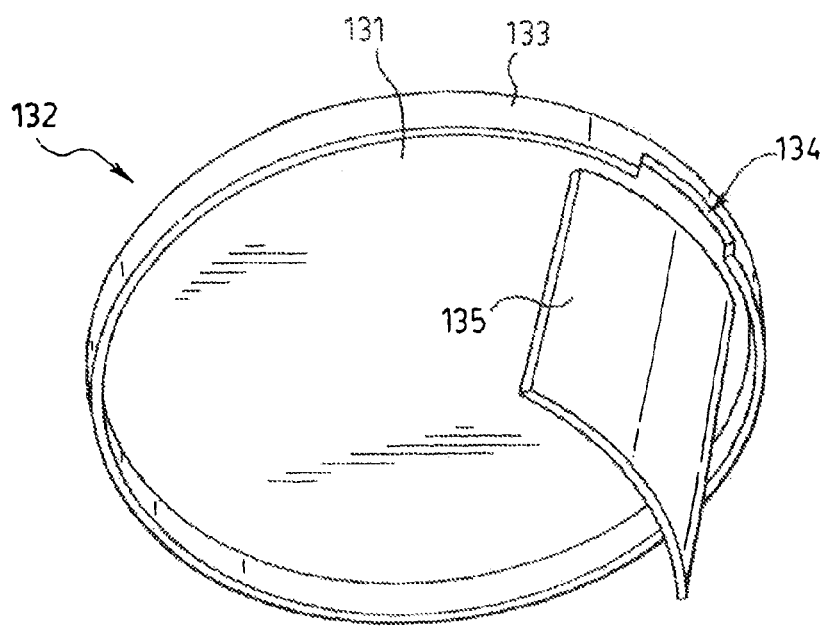
FIG. 10 is a bottom perspective view of a closure cap.
Figure 12:
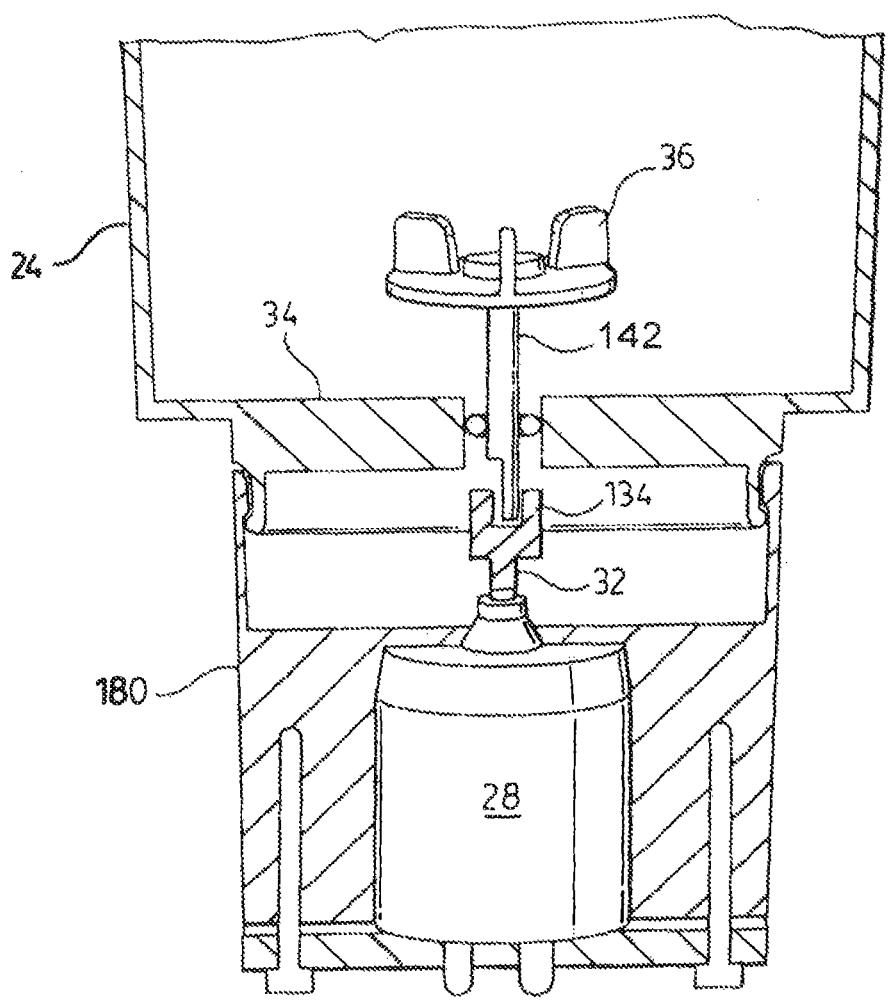
FIG. 12 is a cross-sectional side view of a tank as in FIG. 5 but with a modified snap fit removable motor.

In FIG. 12, tank 24 is identical to that referred to above and carrying an agitating motor 28 secured thereto. A closure cap 132, as shown in FIG. 10, is adapted to close the upper open end of a growing tank in a fluid impermeable manner. The cap 132 has a top 131 and flange 133 substantially the same as that of the lid 26, however, openings which are provided through the lid are not provided through the closure cap 132. The closure cap 132 has a slot 134 in its flange 133 to accommodate the outlet spout 54. A separate internal flange 135 extends downwardly from the top 131 inside from the slot 134 so as to sealably close the outlet opening 53 of the tank 24 by engagement with the inside surfaces of the tank about the outlet opening 53. Thus, with the closure cap 132 applied, the tank 24 is sealably closed.

A sealed package 138 is provided within the tank 24 as is loose powdered material indicated as 140. The replacement bio-generator 136 carries the biomass, nutrients and materials desired to be placed inside the tank 24 for initial start up of any tank 24. The package 138 may be formed from a water soluble film such that on contact with water, the film will dissolve and release the contents of the package. The package may contain one set of components which is desired to be kept separate from the materials 140 which are loose in the tank 24. In this regard, the package 138 may contain materials selected from biomass such as one bacteria in powder or other form ready for growth, a mixture of different biomass sources such as different types of bacteria or initial feedstock or other nutrients which may be in powder, granular, paste or fluid form and may or may not include biomass.

Insofar as the replacement bio-generator 136 is sealed and there is no need to keep the components separated, then it is unnecessary to provide the different components in the separate sealed package 138 and, for example, powdered biomass made by itself merely be placed within the sealed bio-generator as the material 140 with or without nutrients. Alternatively, if two or more components may be desired to be kept separated in the replacement bio-generator 136 or if the replacement bio-generator is not sealed, then the replacement bio-generator may have one or two such packages 138. The packages may be manually opened before use or possibly formed of water soluble film.

A preferred manner of use of the system 10 is now described starting with a system as shown in FIG. 1 but in which the growing tank 24, seen in FIG. 5, is not attached. A replacement bio-generator 136, as shown in FIG. 11, is provided as with a starter mass of bacteria in package 138 and a starter amount of nutrients as material 140. The closure cap 132 is removed. The tank 24 is then coupled to the remainder of the system 10 by coupling the lid 26 onto the tank 24, coupling the tank drain tube 60 to the exit outlet 58, coupling the tank 24 to the rear panel 58 via its mounting bracket 50 and coupling the electrical wiring 40 to the motor 28 via a plug carried on the wiring. Subsequently, the controller 18 is activated and the controller controls the operation of the bio-generator by controlling suitably the operation of the agitating motor 28, the operation of the air fan 92, the operation of the feedstock dispensing unit 88 and the operation of the tank water inlet valve 82 and the drain water valve 79. The controller can control the manner, timing and duration of the operation of these various devices. Typical operation involves, after initial assembly of the bio-generator, adding the desired volume of water to the tank via the tank water inlet port 78, then waiting for a period of time for the water soluble film of the package 138 to dissolve and the nutrients 140 and materials from the package to dissolve or become wetted before activating the motor 28.

For a desired period of time, with operation of the air fan 92 and operation of the agitating motor 28, bacteria is permitted to grow and reproduce within the tank 24, if desired, adding suitable quantities of feedstock and/or water, however, preferably, without the volume of materials in the tank to exceed the capacity of the tank 24. After sufficient biomass has been grown, a quantity of biomass may be dispensed from the tank by raising the fluid level in the tank 24 sufficiently that fluid in the tank 24 will overflow from the tank 24 into the outlet spout 54 and, hence, down the tank drain tube 60 into the drain pan 120 and, hence, via the drain hose 126 to, for example, a grease trap. To better ensure that the discharged bacteria will reach a grease trap, the discharge is flushed from the discharge tube 56 by water from water inlet port 74 as controlled by the controller. With knowledge of the location of the grease trap, a preferred volume of water may be used to flush the discharged bacteria to the grease trap.

The level of the fluid in the tank 24 can be increased to cause overflow by adding additional water via water inlet port 78 and/or by increasing the speed of rotation of the impeller 36 to increase the height of the vortex in the tank. The volume of water provided via the tank water inlet port 78 can be controlled so as to assist control of the extent to which fluid in the tank overflows the tank and is thereby dispensed to the grease tank.

After dispensing a portion of the bacteria containing fluid from the tank 24, bacteria in the bacteria containing fluid remaining in the tank 24 is grown as by adding feedstock and/or water as may be necessary, possibly with some further overflow.

The bio-generator 12 may be used cyclically in each batch to grow biomass and then have a portion of such biomass dispensed. For example, using this method, a certain amount of biomass may be dispensed periodically as, for example, once every 24 hours or less or once every seven days or more or less. However, after a period of time, it is desired that the batch be terminated as with the entirety of the biomass within the bio-generator being removed and a new batch being started with a clean tank and new starting biomass and nutrients.

In this regard and in accordance with the preferred method of operation, after some period of time, say, every one or two weeks or four weeks or six weeks, the operation system is stopped and the existing growing tank 24 is removed. A new replacement bio-generator is provided. The existing growing tank 24 could be thoroughly cleaned and replaced, however. The biomass containing fluid within the used tank 24 is preferably discarded as down the drain pan 120 and may be accomplished manually. A new biomass as, for example, a new starter amount of bacteria and/or nutrients is provided.

The tank drain tube 60 may be reused or could be replaced as a part of a replacement bio-generator. With each preferred disposable replacement bio-generator carrying its own motor, there is no need for the previous motor which may, if desired, be discarded with the originally used tank 24. Alternatively, rather than discarding and disposing of the used tank 24, the used tank and/or its motor may be thoroughly cleaned and reused as, for example, preferably by placing a closure cap 132 from a new replacement bio-generator on the used tank 24 and transporting the used tank and its motor to a location where it can be conveniently cleaned for reuse or recycling in a time and labour efficient and safe manner.

In providing replacement bio-generators 130 with suitable allotments of starter bacteria and/or nutrients, it is possible for the nature and manner and amount of the starter bacteria and/or nutrients to be customized for any particular dispensing system and/or location and/or to customize the same having regard to factors such as ambient time and temperature or control time and temperature which could be preset or could be a condition of the time of the year and/or operational schedules such as activity in a restaurant, plant or other facility, maintenance and the like.

The controller 18 is preferably an electronic control system as is well known commercially and may have various processing units and devices for providing control and input to the controller such that the controller may manage and be controlled to suitably operate the various systems.

Preferably, various sensing mechanisms may be provided as, for example, to sense the level of fluid in the drain pan 120 such that if the level of fluid is above a certain level, then the water inlet valves 79 and 82 may be shut off in an override situation as, for example, to indicate a leak. Similarly, a level sensor may be provided to sense the level of fluid within the tank 24 and/or to sense the concentration of biomass within the liquid within the tank 24. Any such sensors are preferably mounted on the tank lid 26 as to extend downwardly from the tank lid into the tank 24 and, thus, to not impede the ease of coupling and uncoupling of the tank 24 and the lid 26.

The controller is adapted to control the operation of the agitating motor 28 as, for example, to control its on/off operation and/or to control its speed of operation. The controller may control the operation of the air fan 92 as to control its on/off operation and/or to control its speed of operation. The controller may control the solenoids to open or close the inlet valves 79 and 82 and may comprise mechanisms to partially or fully open these valves. The controller may control the operation of the feedstock dispensing unit 88 and may have varying complex control arrangements as to control the duration of time for operation of the dispensing pump having regard, for example, to the quantity of liquids to be dispensed, and to sense and be aware as to the amount of feedstock remaining in the reservoir 94.

While sensors may be used to sense the quantity of biomass in each tank, it is preferred if the controller may have in memory, predetermined estimates of the characteristics of growth of different biomass components having regard to time, temperature, and water added such that the controller may make suitable calculation of optimum conditions for growth, addition of and water and dispensing.

The automated biological growth and dispensing system 10 illustrated in FIG. 1 provides a single growing tank 24. The growing tank 24, according to one preferred embodiment, may have a volume in the range of 0.5 to about 5 liters, more preferably, about 1 liter for relative ease of handling and in order to provide adequate agitation by an agitation motor 28 merely provided in the bottom of the tank 24. As well, having a volume in the range of about 1 liter has the advantage that the agitating motor 28 may comprise a relatively inexpensive motor. Preferred inexpensive electric motors are those which have a power rating in the range of 1.0 to 0.2 watts. For example, one preferred motor is available under the trade name MABUCHI as model number RE-260 RA-18130 which draws about 0.1 amps at 3 volts DC when loaded or about 0.05 amps at 6 volts DC. The use of such a small motor is advantageous to reduce the cost of the motor, to permit the motor 28 to be one which is acceptable to be disposable as, for example, with a used tank 24 and to minimize power consumption. Of course, other motors whether AC motors or stronger motors could be provided having regard to the nature of the tank and the quantities of materials to be received within the tank.

Reference is made to FIG. 12 which shows a schematic cross-sectional view of a lower portion of a tank 24 modified over that illustrated in FIG. 4 so as to show a removable, reusable agitating motor 28 which is provided in a housing 180 adapted to be secured in a snap fit to the lower end of the tank 24. An impeller 36 is provided inside the tank 24 coupled to a driven shaft 142 which extends in a sealed arrangement through the bottom wall 34 of the tank 24. The driven shaft 142 is splined. The entirety of the impeller and its shaft may preferably be of recyclable plastic material and may form disposable components provided with each tank 24.

The agitating motor 28 carries a driver shaft 32 which has a splined socket 134 which is adapted to couple by its sliding axially onto the splined driven shaft 132. Thus, for removal or attachment of a tank 24, the motor 28 via its housing 180 is removably coupled or uncoupled to the bottom of the tank 24.

Figure 13:
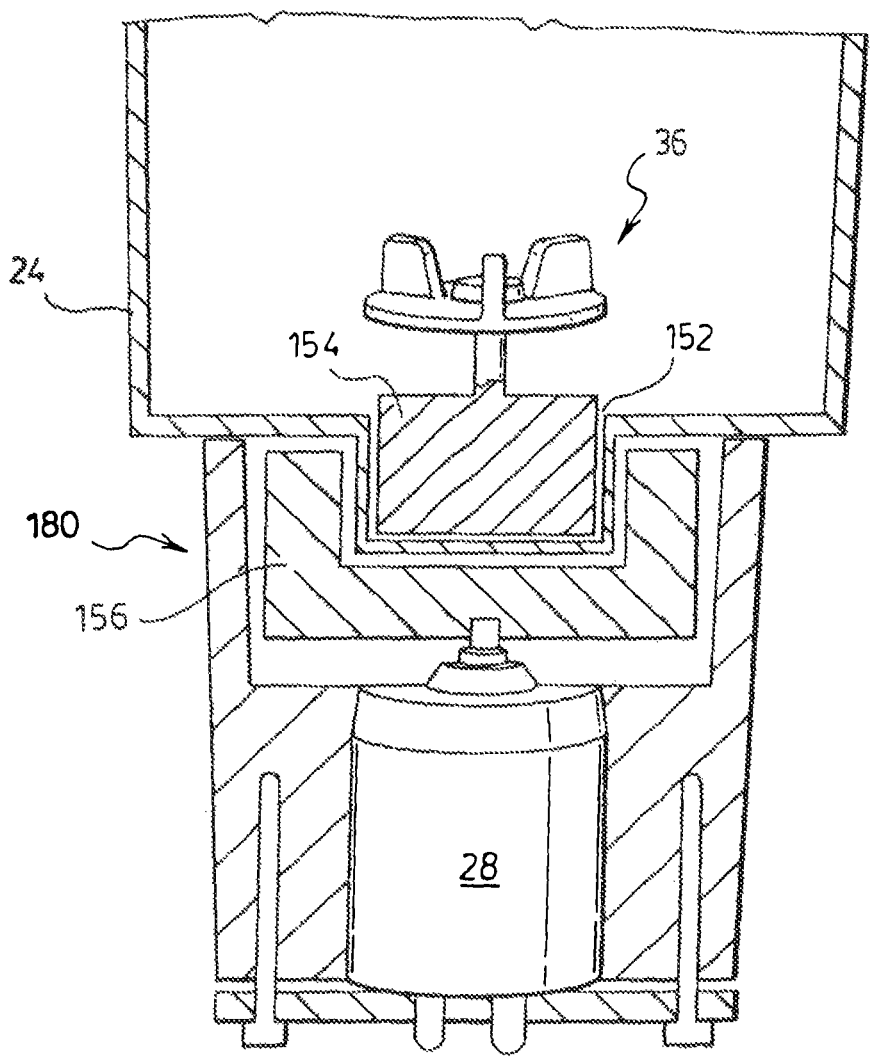
FIG. 13 is a cross-sectional side view of a tank as in FIG. 5 but with a magnetically coupled impeller and motor.

Reference is made to FIG. 13 which shows an arrangement in which a removable impeller 36 is provided within the tank 24 with the impeller 36 being magnetically coupled and rotated by a magnetically coupled removable drive mechanism. In this regard, the lower end of the tank 24 is provided with a cylindrical recess 152 to receive and journal therein the impeller 36 which includes a cylindrical driven magnet 154. An agitating motor 28 is removably coupled via its housing 180 about the bottom of the tank 24 such that the motor 28 rotates an annular driver magnet 156 rotated by a shaft of the electric motor. In a known manner, rotation of the driver magnet 156 by the motor 28 causes the driven magnet 154 and, therefore, the impeller 36 to rotate. Such commercially coupled motors are commercially available. The removable motor may be reused in a sense that when applying a new tank 24, before other materials are placed in the tank, an impeller 36 would be placed in the tank, thereafter, biomass and other materials would be placed in the tank. After use of any one tank, the impeller could be retrieved and cleaned for use in a new tank. Alternatively, since the impellers are relatively inexpensive, a magnetically coupled impeller could be provided with each growing tank, possibly, removably secured in the bottom of a growing tank.

A system in accordance with the present invention can be adapted for use in remote locations without conventional power sources. As a water source, rather than provide water from a conventional pressurized water supply, a water reservoir may be provided at a height above the tank 24 with water either to be dispensed under gravity or via a relatively low power water pump such as a pump which could be used, for example, in the context of the feedstock dispensing unit. To dispense controlled volumes of water under gravity, both a first primary reservoir and a secondary primary reservoir of a predetermined volume may be provided. The second reservoir may be filled under gravity and the entire controlled volume of the second reservoir be dispensed simultaneously down into the tank 24. Solenoids could control flow into and out of the reservoirs. Power for the various components may be provided as from batteries which may be remotely charged as by use of solar panels. Such a remote location may be provided with a remote communication system such as a radio or satellite or cellular phone system to relay signals regarding operation, non-operation and the like.

In accordance with the present invention, preferred usage of disposable, replaceable bio-generators is with a view to minimizing the labour time required to periodically service and restart any particular unit.

In use with standard AC power sources, power service can be either 120 volts or 220 volts which preferably step down to 12 volts DC. For conventional installation, the water source is pressurized water such as from standard utilities.

As to control of the unit in any batch, after the unit has been filled with an initial starter amount of bacteria, nutrients and water, a first cycle will preferably consist of the controller turning on the air fan and the agitating impeller for an initial first time set by the controller. Due to a vortex created by the rotation of the impeller in the tank and the introduction of fresh air from the fan, bacterial growth is promoted. After the initial first time has lapsed, the controller will start the first of a number of repeating dispensing sub-cycles as follows:

1. the air fan and agitating motor 28 are, turned off;
2. the solenoid of the water inlet valve 82 is energized to add a volume of water to the tank 24 as set by the controller (default 250 ml);
3. the air fan 92 and the agitating motor 28 are restarted. The vortex effect formed in the tank by rotation of the impeller 36 will cause some of the fluid in the tank 24 to overflow through the overflow outlet 56 and down the tank drain hose 60,
4. After an elapsed time, (default five minutes), the air fan 92 and motor 28 are shut off.
5. The solenoid of the drain water valve 79 is energized to dispense water and flush any bacteria immediately from the drain hose 60 down through the drain with a volume of water as determined to deliver the biomass to a desired location (default three liters).
6. The feedstock dispensing unit 88 is energized by the controller to dispense a volume of feedstock into the growing tank 24 as predetermined (default 25 ml).
7. The air fan 92 and the agitating motor 28 are turned on for a growing period of time, after which period of time, steps 1 to 7 are repeated.

The extent to which a vortex is formed in the tank by rotation of the impeller and the extent to which the vortex effects may assist in dispensing material from the tank by overflow, can be controlled at least in part by setting the speed at which the impeller rotates. The controller may provide for rotation of the impeller at increased speeds for dispensing as contrasted with lower speeds merely for agitating.

The air gap opening 72 on the tank assists in preventing bacteria media from the tank from being drawn into a portable water source as, for example, in the event of a vacuum being formed at the water source which connects to the inlet valves.

Providing the tanks 24 to have a different tank water inlet port 78 than the drain water inlet port 74 assists in flushing bacteria down the drain when it is dispensed and permits independent filling of the tank as contrasted with a flushing operation.

While the system in accordance with the present invention shows a feedstock dispensing unit 88 as dispensing a liquid, the invention is not so limited and feedstocks which are not in liquid form may be dispensed in controlled quantities into each tank.

In the preferred embodiment of FIG. 1, the growing tank 24 is easily removed and reconnected to the remainder of the system. The lid 26 carries a plurality of connections which need not be disconnected to couple a new tank 24 to the lid 26. Thus, in the preferred arrangement, merely by a single coupling of the tank 24 to the lid 26 and electrical or physical connection of wiring of a motor to the bottom of the tank, the tank 24 is ready for use.

While the invention shows an arrangement in which the tank 24 and lid 26 may be coupled together by relative axial movement, it is to be appreciated that coupling may be accommodated by other movement such as, for example, sliding the tank radially relative to the lid, that is, for example, horizontally as shown in FIG. 1 and that such horizontal movement could also provide a mechanism for simultaneously coupling or uncoupling the motor on the tank to an electrical connection, or of a motor to the tank.

In the preferred embodiments, the air fan 92 is shown as mounted to the lid 26. This is a preferred configuration as it is believed to permit the use of a relatively inexpensive fan to provide air. The fan could, for example, be mounted on the panel 52 separate from the lid and a conduit such as a flexible rubber tube provided to extend from the fan to an opening in the lid 26. In this manner, a single fan is preferred which could provide air to a plurality of tanks.

Dispensing biomass from the tank 24 by overflowing from the tank is believed to be a preferred arrangement as compared to dispensing from the tank by the use of a pump. Providing for overflow by adding water to the tank to raise the level of the tank, itself may be an adequate manner of dispensing portions of the grown biomass. As well, increasing the vortex and, therefore, the level of liquid in the tank with or without the additional water, is another vehicle for dispensing fluid without the use of a pump.

A valving arrangement could be provided so as to open or close an opening in the tank 24 for controlled dispensing of fluid from the tank 24. Any such valve would preferably not form a part of the tank such that the tank could continue to be provided as a separate removable element. An outlet port could be provided from the tank to which a tube drain valve may be readily removable coupled and uncoupled with the drain tube having a solenoid activated valve contained therein for activation as desired to permit materials in the tank to flow under gravity into the tube drain tube with the solenoid is activated.

In the preferred embodiments, the lid 26 substantially closes the tank. This is not necessary. For example, the lid may be located closely above the tank as in engagement therewith or with an air gap therebetween. Sealing of the top of the tank 24 with the lid 26 is preferred to minimize spray and spillage and the like. Arranging the lid 26 so as to not actually engage the tank 24 can facilitate removal or installation of the tank and any motor 28 coupled to the tank 24 or removably engageable with the tank.

FIGS. 14 and 15 illustrate a schematic arrangement in which a gimbaled tank 200 is arranged for tipping about an axis 222 on which it is journalled when the level of fluid in the tank is increased to a point that fluid fills an upper portion 204 of the tank 200 which is asymmetrical about the gimbal axis 222. In this regard, as schematically shown, the tank 200 has an arcuate top edge and a similarly curved lid 26 is spaced upwardly above a tank. The tank is to be journalled about the horizontal gimbal axis 222 as by stub-axles 206 extending from each side of the tank. The lid 26 remains in a fixed position when the tank pivots. The tank 200 is frustoconical over a lower portion 208, however, at an upper portion 204 is asymmetrical with the tank extending further outwardly to the right than to the left as illustrated. When fluid is at a height at or below approximately a level indicated as 210, the tank assumes a vertical orientation as shown in solid lines. When the tank is filled with fluid to a level as indicated as 212, then fluid in the upper portion will cause the tank to rotate clockwise about the axis 222 until such time as sufficient material overflows from the overflow port 56. With, for example, only the wires for the motor connecting the tank to the remainder of the assembly, the tank 200 will be relatively free to rotate to an overflow position in which it may be stopped by a stopper and then, upon dispensing some of the fluid, to rotate back to a relatively stable non-overflow arrangement. The gimbaled tank can be structured such that on the tank tipping to an overflow position, sufficient material will be dispensed so as, for example, to drop the level of fluid in the tank to a level substantially below 210. This will permit additional water and feedstock to be added.

Flushing the material down the drain of the gimbaled tank 200 could be accomplished without causing tipping of the container as by a focused direction of flushing fluid down the outlet tube. As well, mechanical stops such as a solenoid activated locating catch or pin could be provided to secure the tank in an upright vertical position against tipping other than when the catch or pin may be activated and removed.

The lid 26 of FIGS. 1 to 6 may be characterized as a delivery manifold which is removably coupled to the tank 24 via a quick connect and disconnect arrangement which permits by a simple connection or disconnection of the manifold-like lid 26 to the tank 24, the connection and disconnection of the water, air and nutrient delivery systems to the tank 24.

In the preferred embodiment, the motor 28 is provided as an electric motor. It is possible that the motor may be powered other than by electricity. For example, if a supply of pressurized air may be available, then the motor could be an air-driven motor.

In the preferred embodiment, air is delivered into the tank by the air fan 92. The air fan 92 could be replaced by some other source of compressed air as, for example, by pressurized air from an air compressor which may be directed, for example, via a tube downwardly through the tank lid 26. Alternatively, the tank could be provided with air injector ports disposed in the side wall of the tank to direct air directly into the fluid in the tank. To the extent that there may be air injection ports in the side wall of the tank, then it is preferred that the tank incorporate as part of its wall structure air passageways which are open to the top of the tank for coupling to ports in the lid such that by removal and application of the lid 24, connection would be made from between the lid and the passageways in the tank.

Air which may be injected through the side wall of the tank may be injected at relatively high velocity substantially tangential to the side walls of the tank as to assist in agitating fluid in the tank and to create a vortex of fluid in the tank. To the extent that substantial air may be injected in this manner, then the injection of air into the tank can comprise the agitation mechanism which can avoid the need for an impeller within the tank. As another example, air may merely be directed inwardly to the tank through a one-way valve in the bottom of the tank upwardly through the tank to agitate fluid in the tank and to provide oxygen to the liquid in the tank. Insofar as a source of compressed air is readily available, then the compressed air can be used to both drive the compressed air motor to drive an impeller and to inject air into the tank.

In order to provide for additional quantities of biomass which may be desired for any particular application, it is preferred that a multiple of such tanks 24 be provided in any one system 10, that is, the capacity of biomass which can be generated in any time period can be increased by providing a plurality of such tanks, that is, one, two, three, four or more tanks in the same system. This may be accommodated as, for example, by having a single controller 18 to drive a number of individual systems each of which would comprise a bio-generator 12, a feedstock delivery system 14 and a water delivery system 16. A single drain system could be adapted to deliver the overflow from a plurality of tanks 24.

Preferably, each of the modular tanks 24 or 200 may have the same size and configuration, however, this is not necessary and, for certain purposes, tanks may be provided to, for example, have different lengths so as to accommodate different volumes yet have the same top configuration which would permit coupling to standardized lids.

In a system incorporating two or more tanks rather than provide a separate water delivery system and/or separate feedstock delivery system for each of the tanks, insofar as it may be desired to apply similar quantities of water and/or feedstock to each of the tanks, it is possible to merely have the tubes leading from a single feedstock dispensing system and a single water delivery system as being split so as to pass to each of the tanks 24. More preferably, if a single feedstock dispensing system is utilized, then solenoid control valves may be provided in tubes leading to each of the tanks for opening and closing such that the controller can control the precise amounts of feedstock delivered to each of the tanks. Similarly, additional solenoid control water valves could be provided to provide water separately to each tank water inlet port 78 and drain water inlet port 74.

Insofar as the biomass to be grown in different tanks may comprise different species or varieties of biological matter such as different species of bacteria, then it is advantageous in accordance with the present invention to provide different species or mixtures of species in different of the plurality of tanks. For example, rather than having two different types of bacteria in a single tank 24, it may be preferred to have each of the different types in their own separate tank thus providing at least two growing tanks 24. This arrangement better ensures that over time in each batch after that one of the species of bacteria does not grow in preference to the other such that at the end of the period of growth of the biomass for that batch, the biomass does not have a different proportion of the two types of bacteria than initially. Further, in accordance with the preferred operation of the system, the controller may, having regard to input such as temperature, over time to control the addition of feedstock and/or water to any particular tank to thereby adjust and modify the growth in any tank. Insofar as two different tanks may have two different biomass compositions, then the controller may also control timing and amounts of application of the feedstock, water and the relative volumes dispensed from each tank so as to endeavour to place the amount of biomass dispensed from different tanks to bear a predetermined relation from each other.

Where a number of tanks 24 are to be used and replacement bio-generators such as 130 are to be provided including different initial biomass and/or nutrients, then it is advantageous if a system is provided to ensure that an appropriate tank 24 is coupled to an appropriate lid 26 or a portion of that lid. Visual indicia labels, such as with corresponding indicia on the replacement bio-generators 130 and on the appropriate portion of the lid, can be of assistance in ensuring correct correspondence. Similarly, corresponding colour designations may be used. Another advantageous method is to provide the replacement bio-generators 130 not only with visual indicia but also with a mechanical key mechanism which can be applied not only to a tank 24 but also to a lid 26 to receive that tank so as to preclude snap fit assembly of any tank 24 onto any lid 26 but for the desired lid. For example, in this regard, each tank 24 can be provided with a series of radially extending ribs at its upper edge to be received in grooves formed in the flange 66 of the cap with the ribs on the tank 24 to only permit snap fit assembly of that tank onto a lid 26 which has the corresponding slots. For example, a number of such ribs such as ten could be provided on any tank 24 and frangible slots could be provided on any lid 26. By selective removal of the frangible ribs on the tank 24 and selective removal of any frangible tabs covering the slots in the lids 26, a coding arrangement can be provided which would physically prevent the wrong tank 24 from being applied to the wrong lid 26 and, particularly, if the tank may have a factory set allotment of particular biomass to ensure the correct biomass is in the correct tank.

Figure 16:
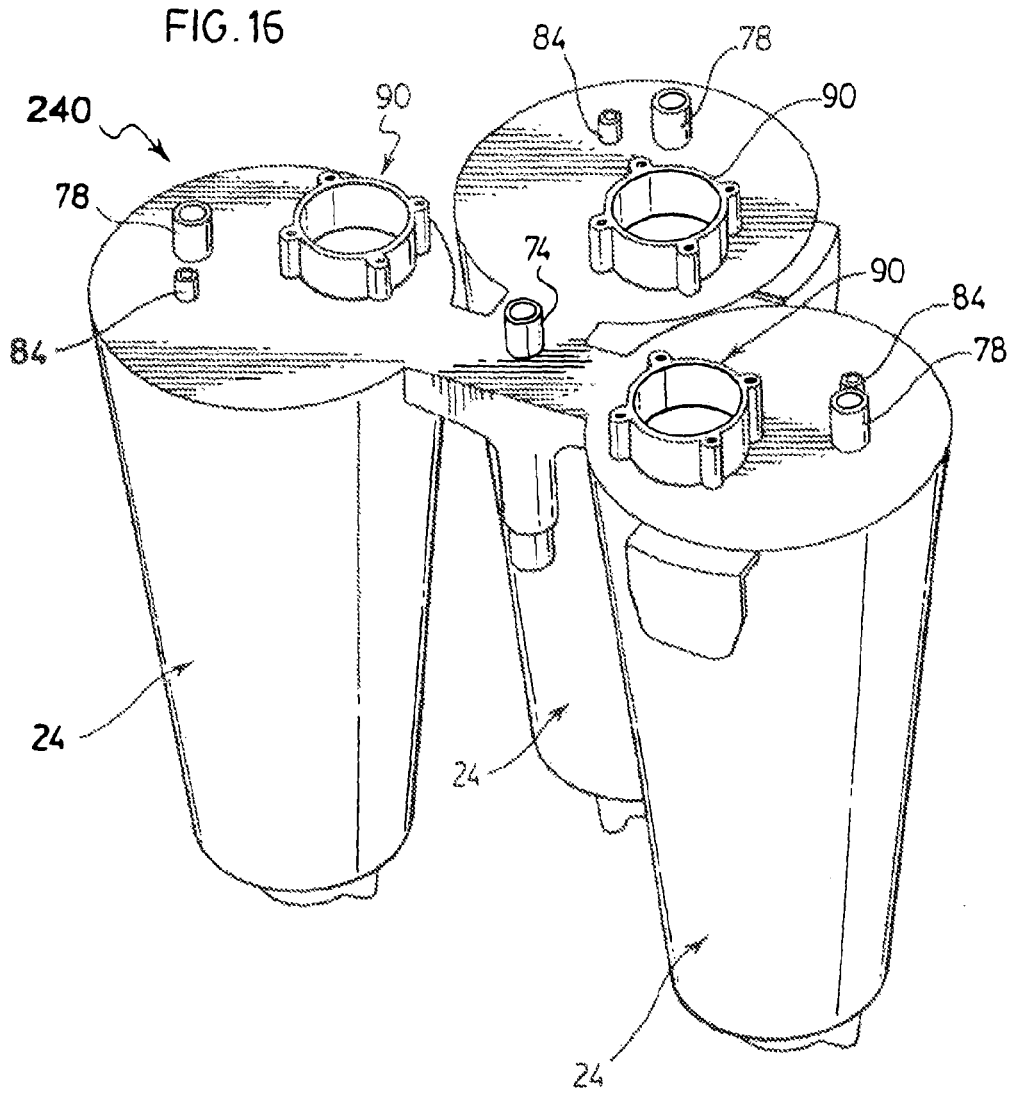
FIG. 16 is a top perspective view showing a tank lid modified over that shown in FIG. 5 as adapted to engage with three tanks.

FIG. 16 shows a modified lid 240 which is adapted to removably receive three modular growing tanks 24 similar to the tanks 24 in FIGS. 1 to 12, however, each having merely an overflow outlet 53 and not the overflow spout 54. The lid 240, shown in FIG. 10, provides a common, three-way overflow spout 54 to connect to each tank and a common drain water inlet port 74. However, the lid 240 has separate tank water inlet ports 78, feedstock ports 84 and separate air fan mounting bases 90 is provided for each tank 24. Each tank 24 is provided with its own agitating motors. While FIG. 16 shows an arrangement with a modified lid 240 adapted for coupling to three modular tanks 24, it is to be appreciated that similar arrangements could be provided to have caps which may couple with one, two, three, four or more such similar modular tanks.

An arrangement in accordance with the present invention which uses more than one tank 24 has the option of being able to be operated in a number of manners. Firstly, as seen in FIG. 16, the three tanks are effectively coupled together in parallel which can accommodate simultaneously growth of bacteria therein. It is preferred that servicing of a unit be carried out at the same time such that each of the tanks would be replaced at the same time and new bacteria initiated at the time of servicing. It is also preferred that bacteria would be grown in each of the tanks simultaneously.

The actual timing of the growth as, for example, by the timing of addition of water and/or nutrients may be the same or may be staggered. Similarly, the dispensing of bacteria containing fluid from the tanks may be simultaneous or may be staggered. Staggered dispensing could be advantageous if, for example, each tank is capable of producing the desired allotment of bacteria containing fluid every three days yet there is a need for dispensing such allotment every day. Thus, the dispensing from the different tanks could be staggered with each tank to dispense on a different day. Depending on the nature of the bacteria, it may be advantageous for optimization of the production of the bacteria to permit each tank to grow for three days before dispensing as contrasted with growing bacteria in each tank for one day and dispensing from each tank every day.

It would also be possible to include a system having more than one tank in which the tanks are coupled in series, that is, with bacteria containing fluid from one or more of the tanks to be directed to one or more of the other tanks where the bacteria may be stored or further grown before being dispensed to a drain system, With such an arrangement, rather than having the tanks arranged at the same height, it may be preferred to have one or more of the tanks at different heights than other of the tanks.

A preferred tank 24 in accordance with the present invention is preferably injection-moulded from plastic material and, therefore, is relatively inexpensive. The plastic material may be selected so as to be recyclable.

The system of the present invention is directed for automated biological growth, more preferably, of bacteria. However, the nature of the biomass to be grown is not limited to bacteria and various other biomass components may be grown in addition to bacteria.

A preferred use of the biomass which is grown is for dispensing to meet a desired use such as removal of grease from grease traps. There are a wide variety of other uses such as digesting oil in oil spills, digesting waste from food, pulp and paper and chemical plants, treatment of human sewage, chemical elements and the like.

While the invention has been described with reference to preferred embodiments, the invention is not so limited. Further aspects and advantages of the present invention will now occur to persons skilled in the art. For a definition of the invention, reference is made to the following claims.

I claim:

1. A batch process for delivering grease digesting bacteria to a drain trap of a drain in a restaurant comprising:

providing a container having a base, a side wall extending upwardly from the base and an exit opening at a height above the base, providing a drain hose for flow under gravity from the exit opening to the drain, providing a fluid in the container at a height below the exit opening, the fluid including the grease digesting bacteria, growing the bacteria in the fluid in the container, providing an impeller in the container rotatable about an axis to discharge fluid impinging on the impeller, rotating the impeller for a period of time at speeds which create and maintain a standing vortex in the container with a height of the standing vortex being below the height of the exit opening, and dispensing fluid from the container to the drain by increasing the speed of rotation of the impeller to increase the height of the standing vortex to the height of the exit opening such that fluid above the exit opening exits the container via the exit opening and flows via the drain hose to the drain.

2. The batch process as claimed in claim 1 wherein the impeller creates the standing vortex by directing fluid radially outwardly into the side wall and up the side wall.

3. The batch process as claimed in claim 2 wherein the side wall is circular in cross-section normal the axis and disposed co-axially about the axis.

4. The batch process as claimed in claim 1 wherein the side wall is circular in cross-section normal the axis and disposed co-axially about the axis.

5. The batch process as claimed in claim 3 wherein the axis is vertical.

6. The batch process as claimed in claim 2 wherein the axis is vertical.

7. The batch process as claimed in claim 1 wherein the axis is vertical.

8. The batch process as claimed in claim 5 wherein the side wall is disposed at a radius about the axis, the radius of the wall increasing as the wall extends upwardly.

9. The batch process as claimed in claim 4 wherein the side wall is disposed at a radius about the axis, the radius of the wall increasing as the wall extends upwardly.

10. The batch process as claimed in claim 5 wherein the side wall is frusto-conical about the side wall increasing in diameter as the wall extends upwardly.

11. The batch process as claimed in claim 1 wherein the fluid includes water.

12. The batch process as claimed in claim 1 wherein the fluid includes nutrients for the bacteria.

13. The batch process as claimed in claim 12 wherein the fluid includes water.

14. The batch process as claimed in claim 12 including providing a population of bacteria and nutrients in the container, and growing the bacteria in the fluid while agitating the fluid by rotating the impeller to maintain the standing vortex in the fluid in the container with a height below the height of the exit opening, and thereafter dispensing fluid including bacteria from the container by increasing the speed of rotation of the impeller.

15. The batch process as claimed in claim 13 including providing a population of bacteria and nutrients in the container, and growing the bacteria in the fluid while agitating the fluid by rotating the impeller to maintain the standing vortex in the fluid in the container with a height below the height of the exit opening, and thereafter dispensing fluid including bacteria from the container by increasing the speed of rotation of the impeller.

16. The batch process as claimed in claim 14 comprising a batch process useful for growing the bacteria comprising repeating a batch cycle comprising:

(a) dispensing a dispensed portion of the fluid including the bacteria from the container by increasing the speed of rotation of the impeller while maintaining a remaining portion of the bacteria in the container, and (b) growing the bacteria in the remaining portion while agitating the fluid by rotating the impeller to maintain the standing vortex in the fluid in the container with a height below the height of the exit opening, with the addition of additional of the fluid and/or the nutrients to the container.

17. The batch process as claimed in claim 15 comprising a batch process useful for growing the bacteria comprising repeating a batch cycle comprising:

(a) dispensing a dispensed portion of the fluid including the bacteria from the container by increasing the speed of rotation of the impeller while maintaining a remaining portion of the bacteria in the container, and (b) growing the bacteria in the remaining portion while agitating the fluid by rotating the impeller to maintain the standing vortex in the fluid in the container with a height below the height of the exit opening, with the addition of additional of the fluid and/or the nutrients to the container.

18. The batch process according to claim 14 including while rotating the impeller to maintain the standing vortex in the container with the height below the height of the exit opening, blowing air downwardly from the top of the container into the container into contact with the fluid in the standing vortex to provide oxygen from the air to the fluid.

19. The batch process according to claim 16 including while rotating the impeller to maintain the standing wave vortex in the tank container with the height below the height of the exit opening, during sub-cycle (b), blowing air downwardly from the top of the container into the container into contact with the fluid in the standing vortex to provide oxygen from the air to the fluid.

20. The batch process of claim 17 wherein the container is a first modular tank,
   the process including repeating the batch cycle a plurality of times with the container comprising a first modular tank, then removing the first modular tank and replacing the first modular tank by a second modular tank identical to the first modular tank,
   providing the fluid and a starter batch of the bacteria into the second modular tank, and repeating the batch cycle a plurality of times with the container comprising the second modular tank.

\* \* \* \* \*